(12) United States Patent
Hargreaves

(10) Patent No.: US 6,537,476 B1
(45) Date of Patent: Mar. 25, 2003

(54) PROCESS OF MAKING A COIL IN A LENGTH OF THERMOPLASTIC TUBING

(75) Inventor: Thomas E. Hargreaves, Buffalo, MN (US)

(73) Assignee: International Polymer Engineering, Inc., Tempe, AZ (US)

( * ) Notice: Subject to any disclaimer, the term of this patent is extended or adjusted under 35 U.S.C. 154(b) by 189 days.

(21) Appl. No.: 09/657,741

(22) Filed: Sep. 8, 2000

(51) Int. Cl.[7] .......................... B29C 53/08; B29C 53/32; B29C 71/00
(52) U.S. Cl. ...................... 264/234; 264/237; 264/334; 264/339
(58) Field of Search ................................ 264/234, 237, 264/334, 339

(56) References Cited

U.S. PATENT DOCUMENTS 4,422,999 A * 12/1983 Mitchell ...................... 264/339
5,287,850 A * 2/1994 Haber et al. ............ 128/203.21

* cited by examiner

*Primary Examiner*—Leo B. Tentoni
(74) *Attorney, Agent, or Firm*—LaValle D. Ptak

(57) ABSTRACT

A method for forming a spring coil in a length of hollow, cylindrical thermoplastic tubing comprises clamping the ends of a predetermined length of cylindrical thermoplastic tubing between first and second opposing spaced clamping members. The first and second clamping members then are rotated relative to one another by a predetermined amount selected to be slightly in excess of 360°, while the mandrels are simultaneously moved toward one another, to shorten the distance between the ends of the length of tubing, while the coil is formed. The clamped tube, with the coil now formed around the mandrels, is rotated and simultaneously heated to the thermosetting temperature of the tubing. After a sufficient time to establish thermosetting of the coil, the heat is removed; the tube is cooled and released from the machine.

8 Claims, 3 Drawing Sheets

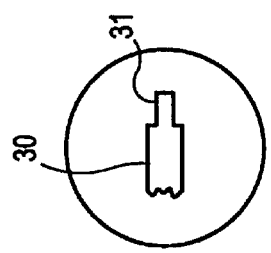
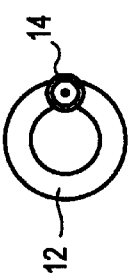
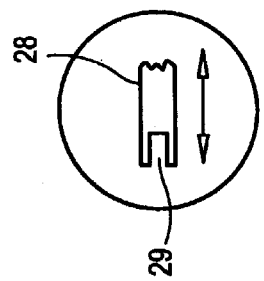
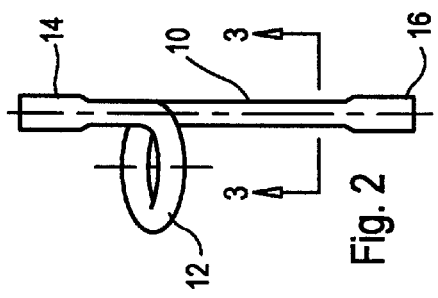
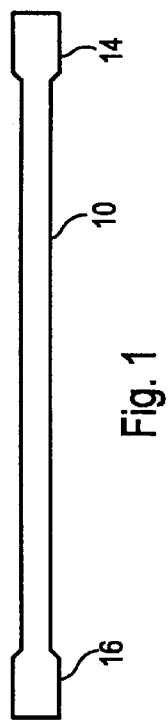
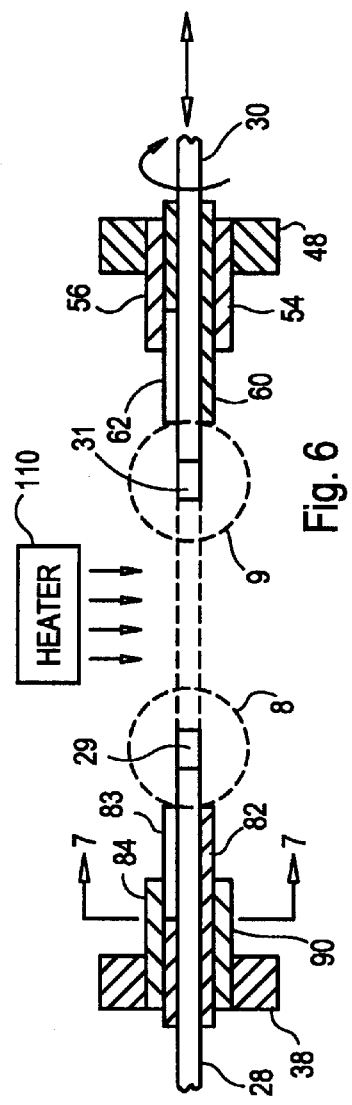
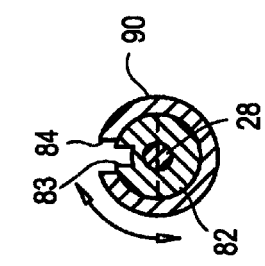

US 6,537,476 B1

PROCESS OF MAKING A COIL IN A LENGTH OF THERMOPLASTIC TUBING

BACKGROUND

Applications exist for dispensing medications by way of inhaler devices. Such devices long have been popular for use by persons with asthma to deliver vapor medications stored under pressure, through a chamber, and ultimately, to an inhaler which is placed in the mouth of the person requiring the medication. The medicine which is dispersed in asthma inhalers, however, is vaporized liquid, which is placed in a pressure dispenser associated with the inhaler. Whenever a dosage of medicine is to be delivered, a valve is momentarily opened to dispense and vaporize the stored liquid for inhalation by the user.

In recent years, experimentation has been undertaken for delivering powdered medicine by way of an inhaler. Particularly promising is the development of insulin powder which may be inhaled, thereby eliminating the need for injected insulin and all of the problems which are attendant with medications which must be injected at frequent intervals. For delivering powdered medication such as insulin powder, the inhaler device must be designed to blow a stream of compressed air through the powder, creating a cloud of tiny medication particles which then may be inhaled from the device.

The Haber U.S. Pat. No. 5,287,850 is directed to a powdered pharmaceutical inhaler mechanism. The device of this patent delivers pressurized air through a coiled tube for dispersing and driving powdered pharmaceutical into the mouthpiece for inhalation by the user. Different parts of the mechanism shown in this patent are designed to be moved from a loading position to a delivery position; and this includes the coiled tube which interconnects these parts. The movement of the tube in this device, however, is quite limited, as is readily apparent from an examination of the device shown in the patent.

For inhaler mechanisms where there is a manual pressurization of a charge of air, different parts of the mechanism need to be moved toward and away from one another a greater distance than the parts of the Haber patent. Typically, such mechanisms require movement of from one-half inch to 1½ inches in order to effect the desired charging and cocking of the mechanism. In such manual pressurization mechanisms, it is necessary to utilize a flexible tube to interconnect the charged air with the delivery portion. This tube must be capable of handling the air pressure charge, as well as extension and retraction as the device is utilized. Because there is a relatively long distance of travel between the parts in the various stages of operation, it has been found that a sufficiently long straight length of plastic tubing tends to bend and rub against other internal parts. This rubbing ultimately causes weakness in the wall of the tube, resulting in failure of the device. Because of the relatively large distance of travel in such a manual charging and cocking mechanism, it also is possible to crimp or kink the tube, which also leads to incomplete or ineffective delivery of the medication, and a failure of operation of the device.

It is desirable to provide a machine and method for forming a thermoplastic tube, with a uniform cross-sectional thickness throughout its length, as a helical spring, which can be extended and released to its thermoset, coiled, biased condition repeatedly for use in manually charged powdered medication delivery systems.

SUMMARY OF THE INVENTION

It is an object of this invention to provide a method for forming a helical coil in a length of hollow cylindrical plastic tubing.

It is another object of this invention to provide a method for forming a helical coil in a length of hollow cylindrical plastic tubing, where the wall thickness of the tubing is uniform throughout its length, including the helical coil.

It is an additional object of this invention to provide a machine for forming a helical spring coil in a length of hollow cylindrical thermoplastic tubing.

It is a further object of this invention to provide a method and machine for forming a thermoset spring coil in a length of hollow cylindrical thermoplastic tubing.

In accordance with a preferred embodiment of this invention, a method and machine form a helical coil in a length of hollow cylindrical thermoplastic tubing. This is accomplished by clamping the ends of a predetermined length of plastic tubing between first and second opposed spaced clamping mechanisms, which may be in the form of first and second sections of a mandrel. The clamping mechanisms, or first and second mandrel sections, then are rotated relative to one another and simultaneously moved toward one another to form a helical coil in the tubing. Where first and second mandrel sections are employed, the helical coil is formed around the mandrels as they move toward one another. Once the coil is formed, the region of at least the coil portion of the tubing is heated to the thermosetting temperature of the tubing to heat-form the coil in the tubing. Following the heating to set the coil, the coil and tubing are cooled; and the spring coil tube is released from the machine.

BRIEF DESCRIPTION OF THE DRAWINGS

FIG. 1 is a side view of a thermoplastic tube segment, which is formed into a thermoset coil by the machine of the preferred embodiment of the invention;

FIG. 2 is a side view of a completed part made by the machine of the preferred embodiment;

FIG. 3 is a cross-sectional view, taken along the line 3—3 of FIG. 2;

FIG. 6 is a cross-sectional detail of a portion of the embodiment shown in FIGS. 4 and 5;

FIG. 7 is a cross-sectional view taken along the line 7—7 of FIG. 6;

FIG. 8 is an enlarged detail of the portion encircled as "8" in FIG. 6; and

FIG. 9 is an enlarged detail of the portion shown encircled as "9" in FIG. 6.

DETAILED DESCRIPTION

Reference now should be made to the drawings, in which the same or similar components have the same reference numbers throughout the different figures. FIG. 1 is a side view of a short length of elongated flexible tube or conduit, which is intended to be formed into a coiled spring conduit member designed to interconnect two different parts of a powdered medicine delivery inhaler mechanism.

An inhaler device, in which the tube shown in FIGS. 1, 2 and 3, is used, is subjected to air pressure of approximately 80 psi when air is released through the dispenser device and the tube 10. The tube 10 of FIG. 1 is formed from thermoplastic material, which may be extruded and then subsequently heat formed. Initially, extruded tubular material, having the desired internal and external diameters, is cut into the desired length; and segments 14 and 16, at both ends, are flared by means of heat forming insert mandrels. The manner in which this is accomplished is not important to an understanding of the present invention. It is to be noted, however, that the starting material for use with the machine described subsequently is the tube 10, shown in FIG. 1, with the enlarged or flared segments 14 and 16 on the ends. The flared segments are selected to have an internal diameter which is greater than the uniform internal diameter of the main body 10 of the tube, for purposes of interconnecting the finished product in an inhaler with a uniform internal diameter airflow passage throughout the length of the entire mechanism, including the portions to which the flared end segments 14 and 16 are attached.

In order to form a substantially single-turn helical coil 12, thermoset into the shape shown in FIG. 2, from the straight length of tube 10 of FIG. 1, the machine shown in FIGS. 4 through 9 is employed. This machine is designed to simultaneously produce six thermoset coiled spring tube members of the type shown in FIGS. 2 and 3 with each cycle of operation. The finished product, as shown in FIGS. 2 and 3, is a thermoplastic tube 10 with a uniform cross-sectional thickness throughout its length. The tube is thermoset formed as a helical spring which may be extended and released repeatedly to its thermoset-biased coiled condition, for use in manually-charged, powdered medication delivery systems.

Figure 4:
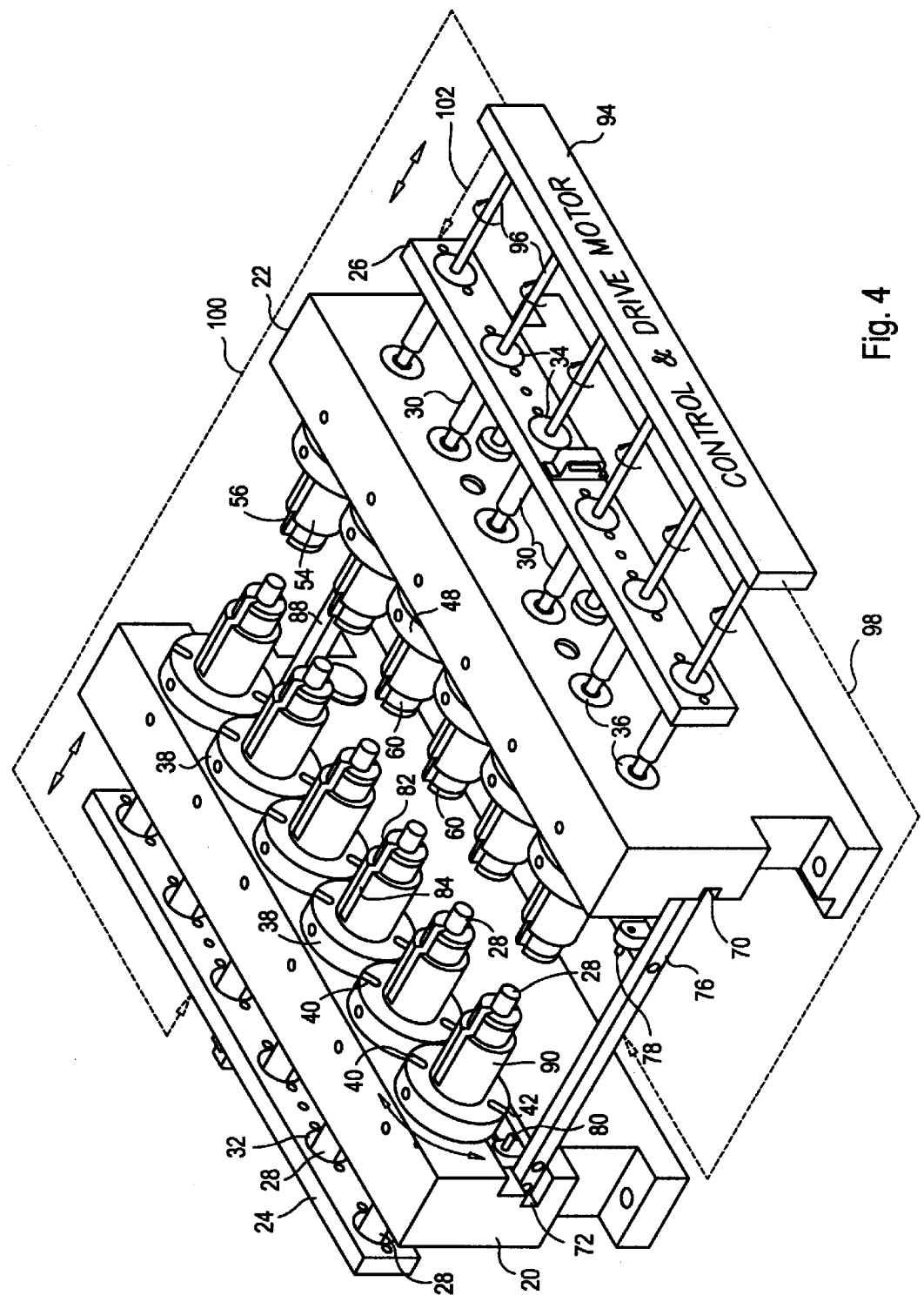
FIG. 4 is a perspective view of a preferred embodiment of the invention.
Figure 5:
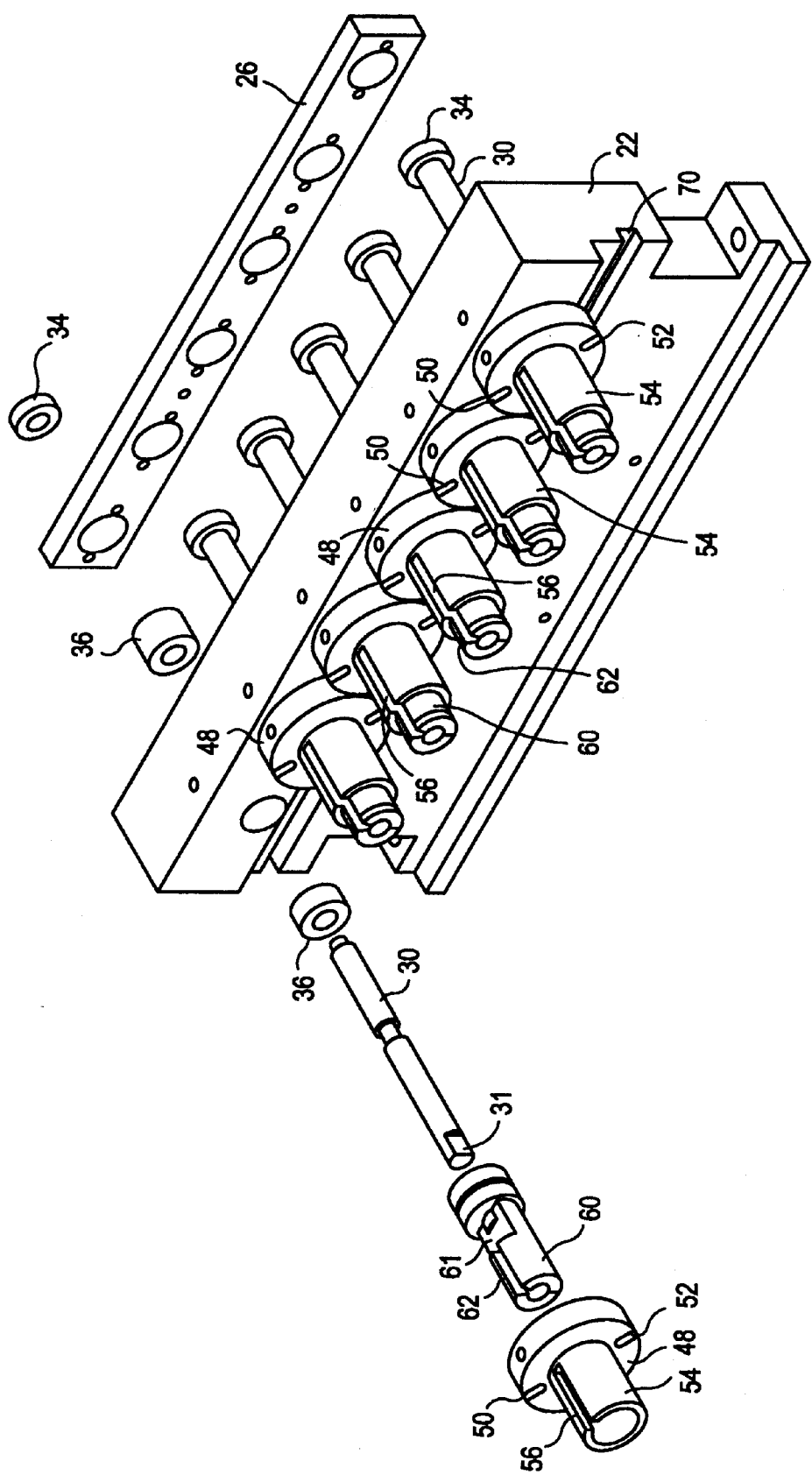
FIG. 5 is an exploded view of a portion of the embodiment shown in FIG. 4.

FIG. 4 is a top perspective view of the primary operating components of the machine of the preferred embodiment used to form the product shown in FIG. 2. Some conventional mechanisms, which may be associated with the machine of FIGS. 4 and 5, have not been shown in order to more clearly present the features which are unique to the operation of the preferred embodiment of the invention.

Basically, the machine includes two spaced-apart parallel mounting blocks 20 and 22, which are secured to a machine base (not shown) in any suitable manner. The blocks are spaced a uniform distance apart; and each of them includes six aligned, equally spaced support bearings for rotating mandrels. The mandrels, in turn, are supported in a pair of movable, bearing support members 24 and 26 for the blocks 20 and 22, respectively. Six mandrels 28 extend through bearings 32 in the member 24; and a corresponding six mandrels 30 extend through bearings 34 in the mandrel support member 26.

As shown in both FIGS. 4 and 5, the mandrels 30 also slidably extend through the bearings 36 in the main support block 22, as well. Similar bearings (not shown) in the support block 20 are used for allowing pivotal rotation of the mandrels 28 in that support block for either or both sets of mandrels 28 and 30. The mandrel support members 24 and 26 for either or both sets of mandrels 28 and 30 are arranged to be moved toward and away from the blocks 20 and 22, respectively, through means of a suitable electromechanical system 94. This is diagrammatically illustrated in FIG. 4, by means of the dotted lines 100 and 102 interconnecting the mandrel support members 24 and 26 with a control and drive motor unit 94.

In the operation of the machine, at the beginning of each cycle, six pre-formed plastic tube sections of the type shown in FIG. 1 are dropped into aligned slots 62 and 83, formed on the upper surfaces of opposite sleeves 60 and 82, respectively, which surround the mandrels 30 and 28, as shown most clearly in FIG. 6. One of the pre-formed lengths of tube 10, with the flared end segments 14 and 16, is placed in each of these opposing sleeves in the slots on the top of the mandrels 30 and 28, in each of the six different positions of the six-unit machine shown in FIG. 4. Each of the different positions are identical; and one of them is diagrammatically illustrated in FIG. 6.

FIG. 5 illustrates, in an exploded view, the portions of the sleeves and operating parts which are associated with one of the mandrels 30. It should be noted that each of the mandrels 30 are identical, and that the corresponding parts which are associated with those mandrels are identical. For that reason, only one has been shown in exploded detail. Similarly, the mandrels 28 are surrounded with sleeves and operating collars which are identical to one another, and are identical to the one shown in exploded view in FIG. 5. In order to avoid cluttering the drawing with unnecessary details, only one of the mandrel and sleeve sets is shown in exploded detail; and only a partial cross section of some of the operating features is shown in FIG. 6.

When a part 10 is dropped into the slots 62 and 83, as shown in FIGS. 5 and 6, the flared end rests on a wider flat portion 61 on the sleeve 60 (and a corresponding flat portion on the sleeve 82) with the main body of the tube 10 which is located between the end segments 14 and 16 extending through the narrower slot 62, for example, in the sleeve 60. An identical construction on all of the other sleeves on both sides of the machine is employed; so that the tube 10 extends through the narrow slots 60 on the machine portion carried by the block 22, and a similar set of slots 83 carried by the sleeves 82 on the block 20.

FIG. 7 is a cross-sectional view of this portion of the machine, which illustrates the orientation of the sleeve 82 and its slot 83, with respect to the mandrels 28. Again, a similar cross section taken on any of the other sleeves and mandrels, on both sides of the machine, is identical to the one shown in FIG. 7.

In order to lock the thermoplastic tube section 10/14/16 into place for effecting a subsequent rotating operation, a second sleeve is provided at each of the mandrel positions. This is a larger sleeve, 90 for the mandrels associated with the block 20, and 54 for the mandrels 30 associated with the block 22. The cross-sectional views of FIGS. 6 and 7 illustrate the general orientation of the locking sleeves 90 and 54 with respect to the other parts.

After the tube section 10 of FIG. 1 is placed in the slots on the smaller sleeves 82 and 60, as described above, the locking sleeves 90 and 54 are rotated to cause the open gap, such as the gap 84 shown in FIGS. 6 and 7, to rotate over and close the opening over the top of the flanges 14 and 16. The flanges 14 and 16 stick up just slightly above the upper diameter projection of the sleeves 60 and 82; so that when this rotation of the sleeves 90 and 54 is effected, a vice-like clamping action is provided to tightly grip the end segments 14 and 16 in place, and hold them against any rotation of the tube 10 during the next cycle of operation of the machine.

To effect the clamping of the end segments 14 and 16, a rectangular sliding bar assembly, including a pair of spaced-apart horizontal end members 76 and 88, which are interconnected by elongated side members (not shown) is provided. This rack slides in facing slots 70 and 72 in the support blocks 22 and 20, respectively, and. is operated by the control and drive motor mechanism 94 at the beginning and end of each cycle to reciprocate back and forth, as indicated by the double-ended arrow at the left-hand end of FIG. 4. Once all of the tubes 10 are in place as described above, the rack 76/88 is moved toward the right, as viewed in FIG. 4, to cause six spaced engaging pins 78, on the right-hand end side of the rack 76, and a corresponding set of six engaging pins 80 on the left-hand side of the rack, to engage corresponding slots 52 and 42 located, as is most readily apparent in FIGS. 4 and 5, on the lower sides of circular operators 48 and 38 which are fixedly attached for rotation with the sleeves 54 and 90, respectively. When the rack 76/88 moves toward the right, as seen in FIG. 4, the operators 48 associated with the sleeves 54 are rotated clockwise (as viewed in FIG. 5); and the operators 38, associated with the sleeves 90 in the support block 20, are operated counterclockwise (as viewed in FIG. 4) to rotate over the openings in the ends of the slots 62 and 83 and effect the clamping of the flanges 14 and 16, as described above. The rack 78/88 remains in its rightmost position for the duration of the next portion of the cycle of operation. It should be noted, however, that for the operation just described, the pins 78 and 80 engage the slots 52 and 42, respectively, to effect the rotation. This causes a second set of slots (located 180° from the slots 42 and 52 engaged by the pins 78 and 72) to be rotated into position for subsequent engagement for rotating the assembly back to the starting position, once a complete cycle of operation has taken place. For the purposes of the next portion of the ensuing discussion, however, it should be noted that the rack 78/88 moves from the position shown in FIG. 4 toward the right (as shown in FIG. 4), as described above, and remains there until it is time to commence a new cycle of operation.

After the flanges 14 and 16 are locked into place, the control and drive motor mechanism 94 commences rotation of the mandrels 30, through a set of drive shafts, while the mandrels 28 remain in a fixed or non-rotating condition. At the same time, the control and drive motor 94 moves the mandrel support members 24 and 26 toward the blocks 20 and 22, respectively, in synchronism with the rotational force applied through the drive shafts 96 to the mandrels 30 to cause a coil 12 to be formed in the center of the pre-formed cut length of thermoplastic tubing 10 of FIG. 1. In FIG. 2 the coil 12 is shown offset from the center, but in reality, the coil 12 will form at the center of the tube 10 because of the uniform wall thickness and strength of the material.

The movement of the mandrel support blocks 24 and 26, toward one another, is at a rate to accommodate for the reduction in length between the ends of the tube 10 as the coil 12 is formed in it. The coil 12 forms around the path of the mandrels 28 and 30; and in fact, as they approach one another, the coil 12 is wound around the mandrels 28 and 30.

At the end of the rotation to form the coil 12 (chosen to be slightly more than 360° of relative rotation between the mandrels 30 and 28), the mandrel ends 29 and 31 engage one another. FIGS. 6, 8 and 9 show details of this portion of the mechanism. The mandrels 28 have a slot 29 formed in their end; and the mandrels 30 have a flat projection 31 formed in the end, which mates with the slot 29. As a consequence, when the mandrel 30 is moved into engagement with the end of the mandrel 28, the flat projection 31 extends into the slot 29. Continued rotation of the mandrel 30 under control of the drive motor 94, through the shaft 96, now causes the entire assembly of joined mandrels 30 and 28 to rotate together at the same rate. This occurs immediately after the coil is formed in the tube 10.

During the time mandrels 28 and 30 are engaged (as indicated in dotted lines in FIG. 6) for rotation together, hot air at a sufficiently high temperature to exceed the thermosetting temperature characteristics of the plastic used in the tube 10, is applied to the coils 12 through a heater 110. The coils 12 rotate in the region of the hot air applied from the heater 110; and this rotation in thermosetting heat is effected for a length of time sufficient to cause the thermosetting formation of the coil 12. Once thermosetting of the coil 12 in the tube 10 has been completed, heat application from the heater 110 is discontinued. Continuous rotation of the mandrels 30 and 28 together is effected; and if desired, cooling air may be blown across each of the coils 12 in a conventional manner (not shown) to effect a more rapid cooling down of the parts. Once the parts are sufficiently cooled, the rack 78/88 is operated by the control and drive motor mechanism 94, through the control link indicated in dotted lines 98, to move back toward the left and to rotate the sleeves 54 and 90 back to the relative positions shown in FIGS. 4, 5 and 7. The slots 62 and 84 once again are opened. Continued rotation of the mandrels 30 and 28 then causes the assembly, including the sleeves 54, 90, 60 and 82, to rotate where the openings 62, 83, 56 and 84 are pointed downwardly; so that gravity allows the finished parts of the type shown in FIG. 2 to drop out of the open slots. Rotation another 180° back to the position shown in FIGS. 4, 5 and 7 is effected. Rotation of the mandrels 30/28 ceases; and the mandrel support members 24 and 26 are moved back to the positions shown in FIG. 4 by the control and drive motor mechanism 94. The finished parts drop free. The system now is ready for a new cycle of operation, repeating all of the steps which have been described above.

The foregoing description of a preferred embodiment of the invention is to be considered as illustrative and not as limiting. Various changes and modifications will occur to those skilled in the art for performing substantially the same function, in substantially the same way, to achieve substantially the same result without departing from the true scope of the invention as defined in the appended claims.

What is claimed is:

1. A method for forming a coil in a length of cylindrical thermoplastic tubing including the steps of:
    clamping the ends of a predetermined length of cylindrical thermoplastic tubing between first and second opposing spaced clamping members;
    rotating the clamping members relative to one another and simultaneously moving the clamping members toward one another by a predetermined distance to form a coil in the tubing;
    heating at least the coil of the tubing to its thermosetting temperature for a predetermined period of time;
    cooling the tubing; and
    releasing the tubing from the clamping members.

2. The method according to claim 1 wherein the steps are performed sequentially in the order named.

3. The method according to claim 2 wherein the clamping members are rotated together during the heating step for uniformly heating the helical coil of the tubing.

4. The method according to claim 3 wherein the clamping members are rotated together during the cooling step.

5. The method according to claim 4 wherein the step of releasing the tubing includes moving the mandrels apart relative to one another.

6. The method according to claim 1 wherein the clamping members are rotated together during the heating step for uniformly heating the helical coil of the tubing.

7. The method according to claim 6 wherein the clamping members are rotated together during the cooling step.

8. The method according to claim 1 wherein the step of releasing the tubing includes moving the mandrels apart relative to one another.

* * * * *